(12) United States Patent
Buchlovic

(10) Patent No.: US 9,695,147 B2
(45) Date of Patent: Jul. 4, 2017

(54) PROCESS FOR THE PREPARATION OF PERAMPANEL

(71) Applicant: TEVA PHARMACEUTICALS INTERNATIONAL GMBH, Jona (CH)

(72) Inventor: Marian Buchlovic, Levice (SK)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 14/907,374

(22) PCT Filed: Jul. 24, 2014

(86) PCT No.: PCT/US2014/048034
§ 371 (c)(1),
(2) Date: Jan. 25, 2016

(87) PCT Pub. No.: WO2015/013520
PCT Pub. Date: Jan. 29, 2015

(65) Prior Publication Data
US 2016/0176842 A1    Jun. 23, 2016

Related U.S. Application Data

(60) Provisional application No. 61/858,368, filed on Jul. 25, 2013, provisional application No. 61/927,424, filed on Jan. 14, 2014, provisional application No. 62/016,797, filed on Jun. 25, 2014.

(51) Int. Cl.
| | | |
|---|---|---|
| *C07D 213/22* | (2006.01) | |
| *C07D 401/04* | (2006.01) | |
| *C07C 253/30* | (2006.01) | |
| *C07D 213/38* | (2006.01) | |

(52) U.S. Cl.
CPC .......... *C07D 401/04* (2013.01); *C07C 253/30* (2013.01); *C07D 213/22* (2013.01); *C07D 213/38* (2013.01)

(58) Field of Classification Search
CPC .................................................. C07D 213/22
USPC ................................................. 546/257, 258
See application file for complete search history.

(56) References Cited

U.S. PATENT DOCUMENTS

| | | | |
|---|---|---|---|
| 4,072,746 A | 2/1978 | Lesher et al. | |
| 6,949,571 B2 * | 9/2005 | Nagato ................ | C07D 213/64 514/333 |
| 7,524,967 B2 | 4/2009 | Koyakumaru et al. | |
| 8,304,548 B2 | 11/2012 | Kayano et al. | |
| 8,742,118 B2 | 6/2014 | Fontana et al. | |
| 2010/0016603 A1 | 1/2010 | Sonoda et al. | |

FOREIGN PATENT DOCUMENTS

WO    WO 2014/023576    2/2014

OTHER PUBLICATIONS

International Search Report and Written Opinion for International Application No. PCT/US2014/048034, mailed on Jan. 7, 2015.
Charles McElhinny, Jr., et al., A Practical, Laboratory-Scale Synthesis of Perampanel, Synthesis, vol. 44, No. 01, Nov. 4, 2011.
Dong-Ung Lee, et al., Verlust ortho-standiger Substituenten aus Phenylacetamid-Ionen, Archiv Der Pharmazie, vol. 321. No. 5, 1988, pp. 265-272(English-language abstract provided).

* cited by examiner

*Primary Examiner* — Patricia L Morris
(74) *Attorney, Agent, or Firm* — Andrews Kurth Kenyon LLP

(57) ABSTRACT

The present invention provides intermediates useful for the synthesis of Perampanel and processes employing said intermediates for preparing Perampanel. The invention also provides processes for making the intermediates, crystalline forms of the intermediates and the use of the crystalline forms for preparing Perampanel.

5 Claims, 9 Drawing Sheets

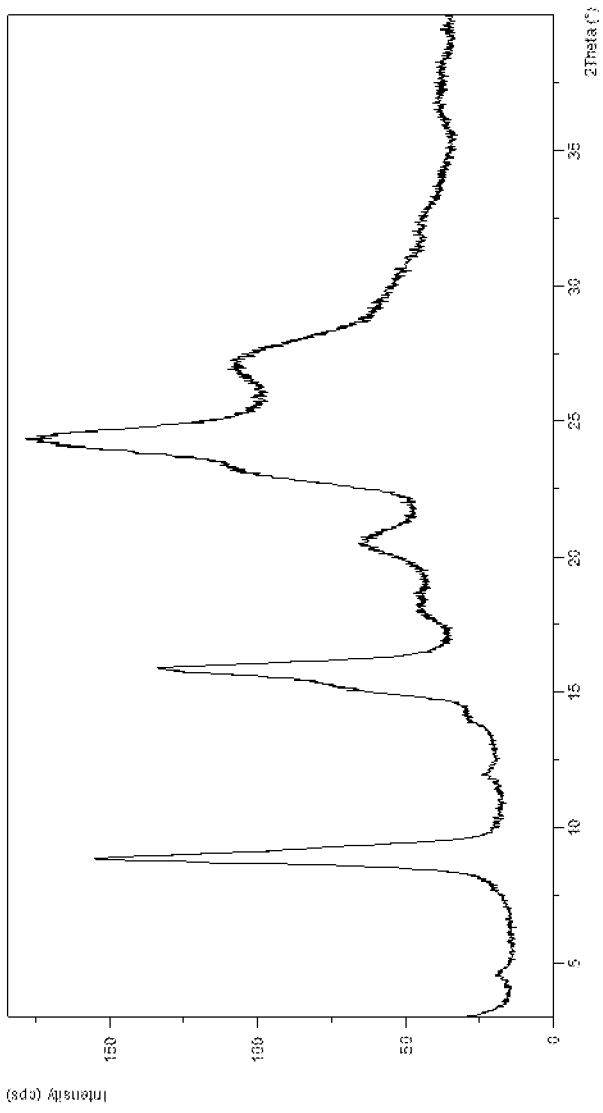
Figure 1: A powder XRD pattern of crystalline Perampanel form II.

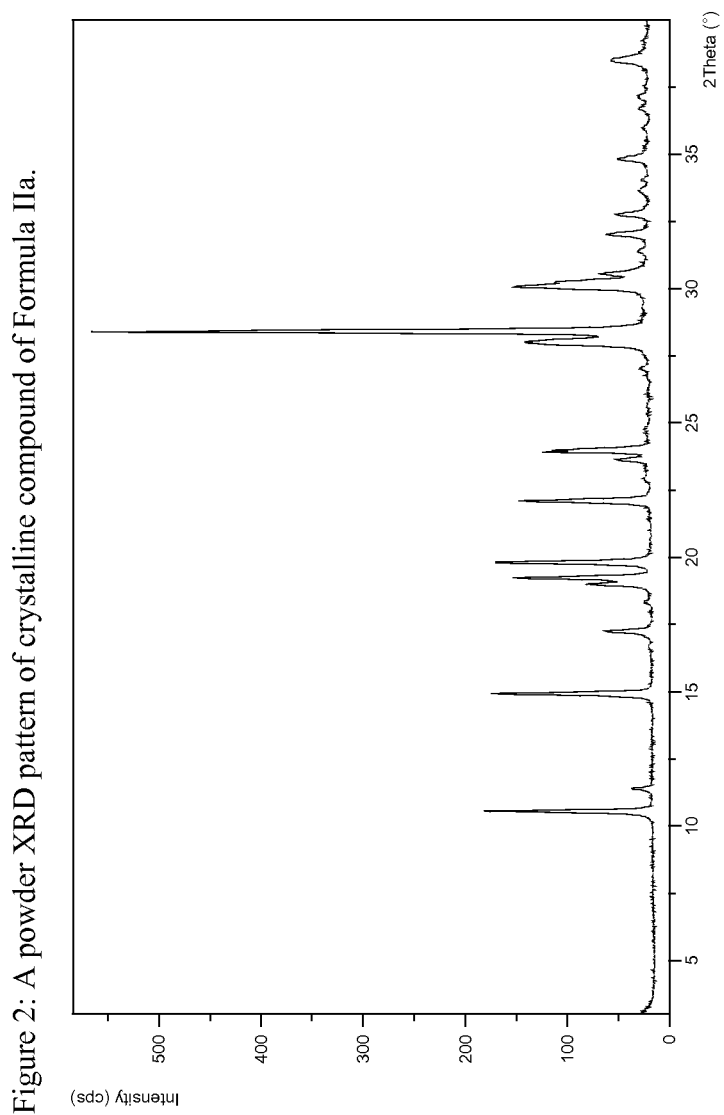
Figure 2: A powder XRD pattern of crystalline compound of Formula IIa.

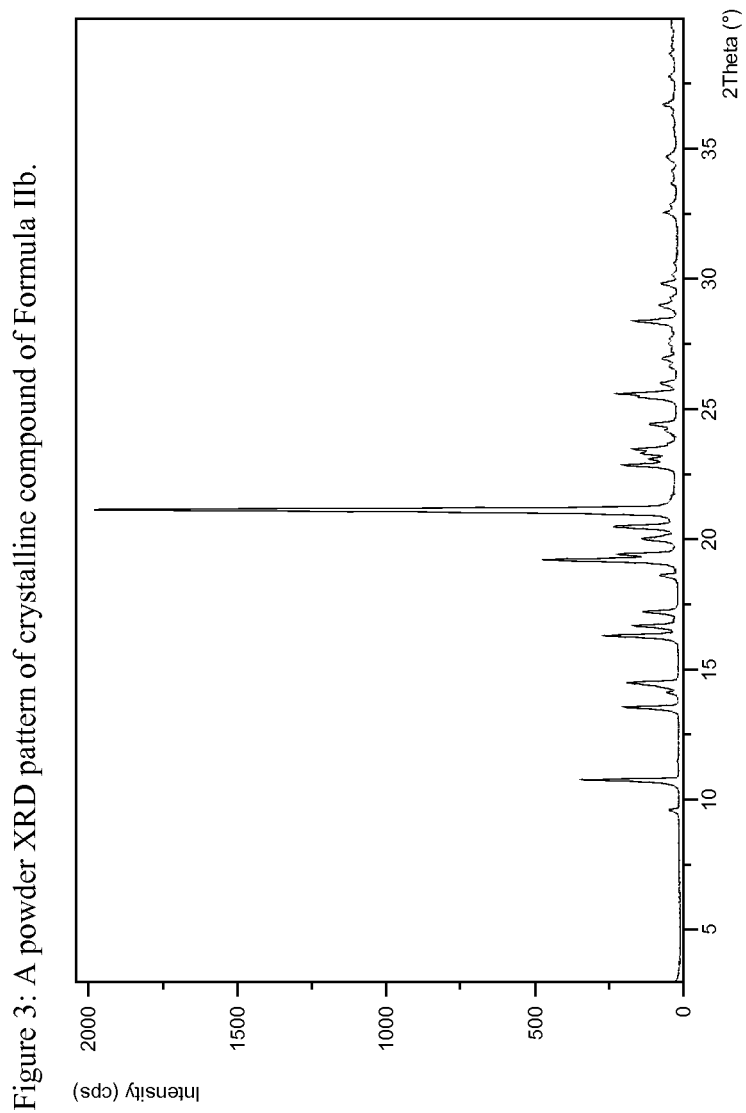
Figure 3: A powder XRD pattern of crystalline compound of Formula IIb.

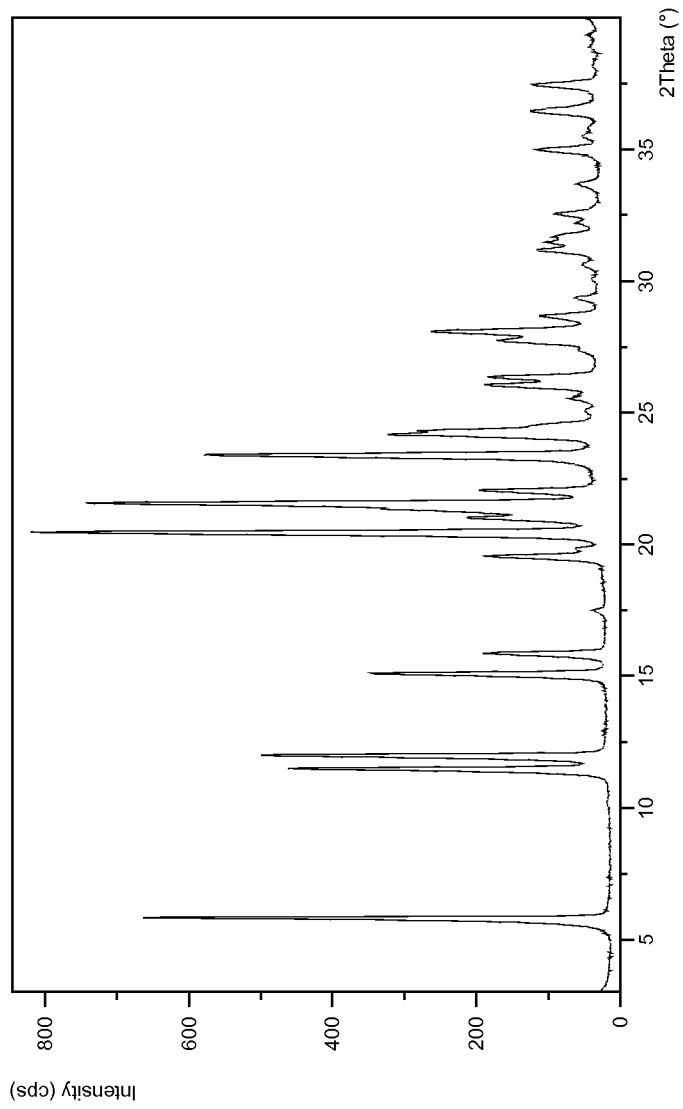
Figure 4: A powder XRD pattern of crystalline compound of Formula IIIa.

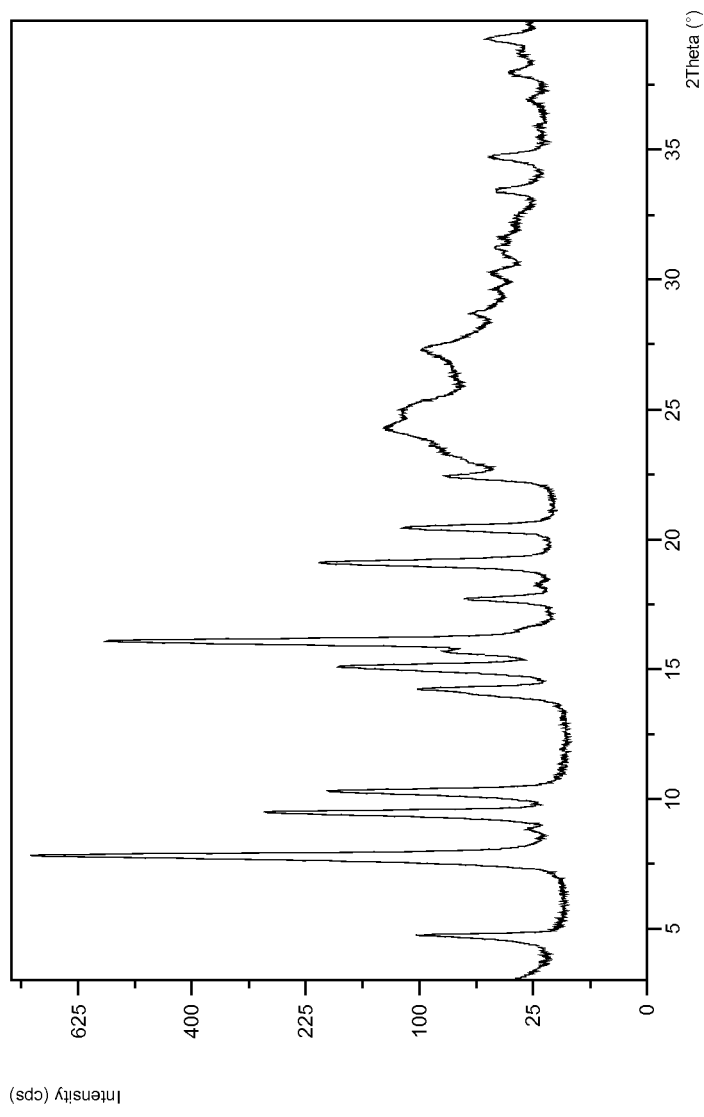
Figure 5: A powder XRD pattern of crystalline Perampanel form I

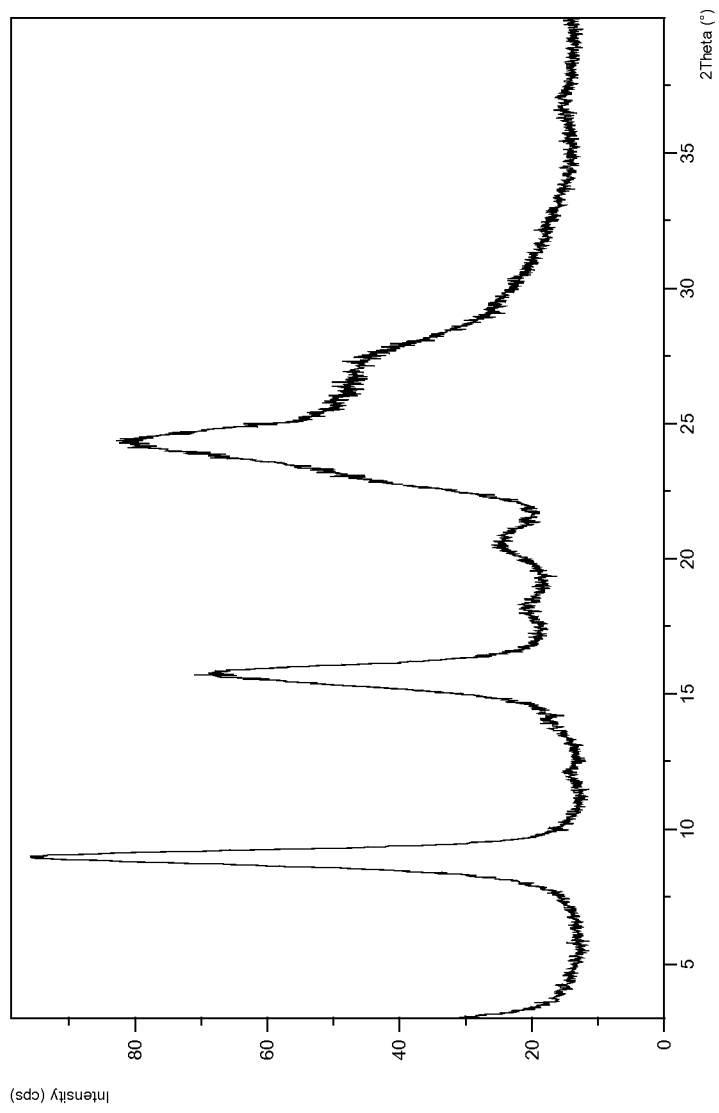
Figure 6: A powder XRD pattern of polymorphic pure crystalline Perampanel form II

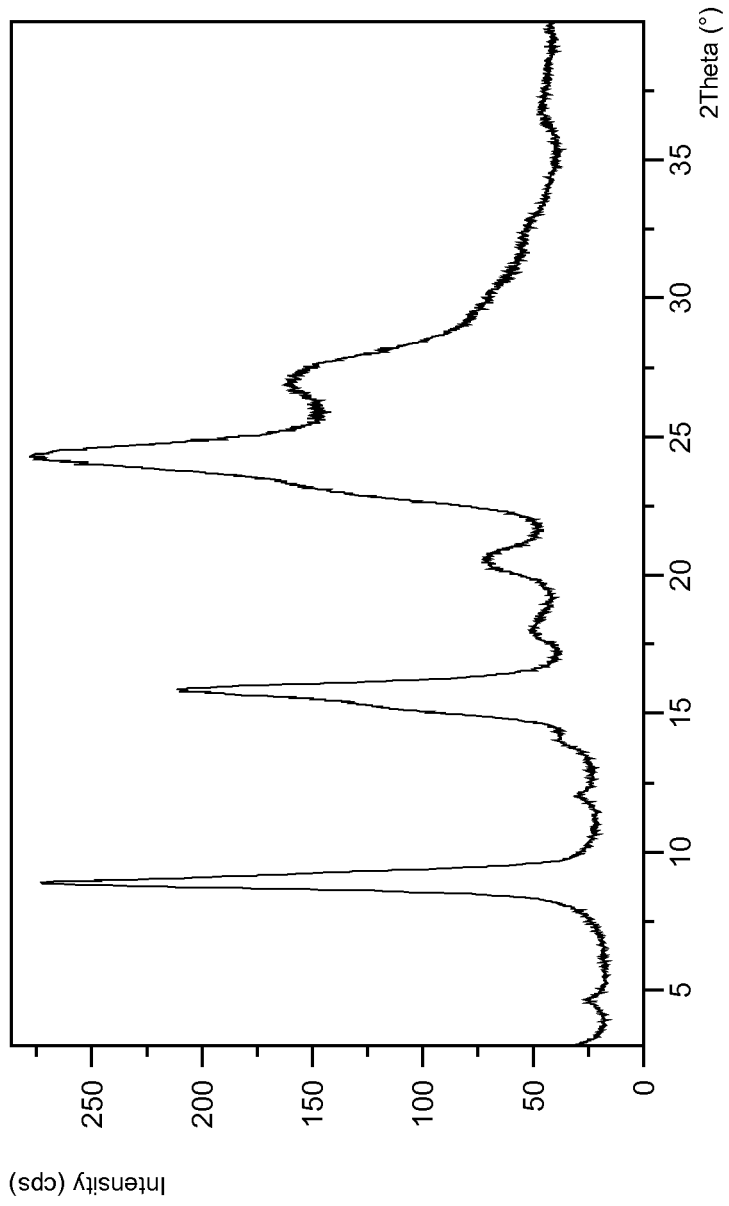
Figure 7: A powder XRD pattern of crystalline Perampanel form II obtained in example 13:

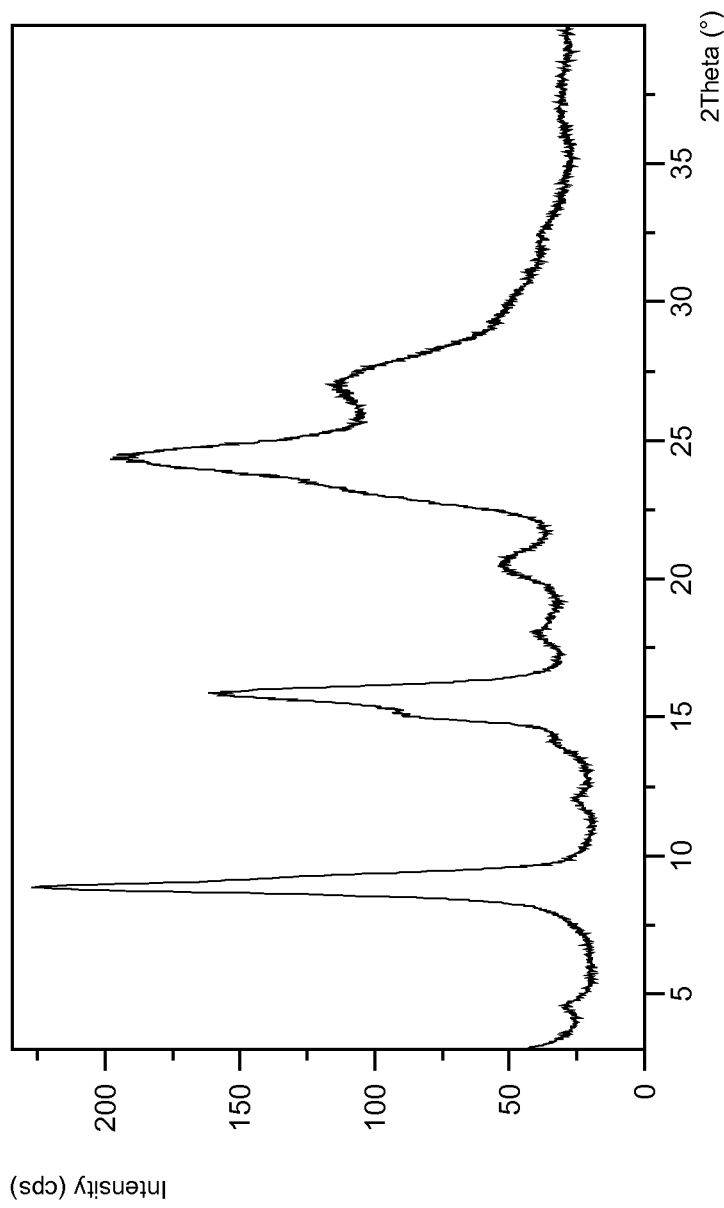
Figure 8: A powder XRD pattern of crystalline Perampanel form II obtained in example 14:

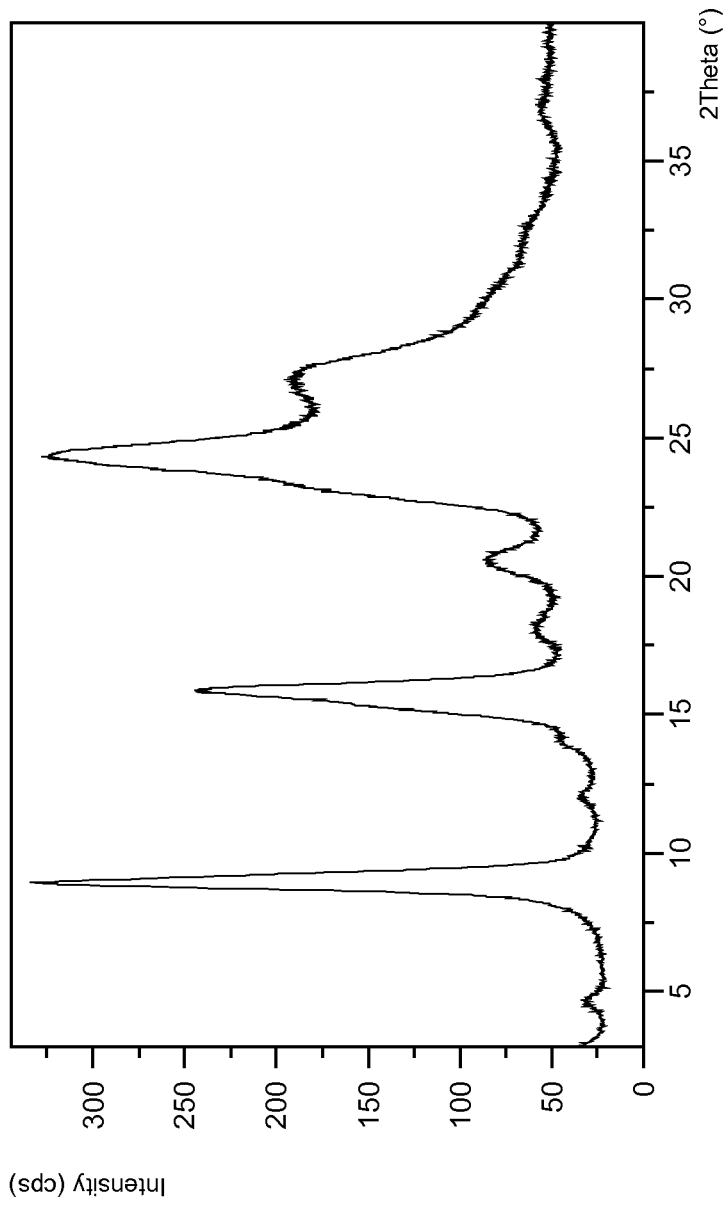
Figure 9: A powder XRD pattern of crystalline Perampanel form II obtained in example 15:

PROCESS FOR THE PREPARATION OF PERAMPANEL

CROSS REFERENCE TO RELATED APPLICATIONS

This patent application is a U.S. National Phase of PCT/US2014/048034, filed on Jul. 24, 2014, and claims the benefits of U.S. Provisional Application Nos. 61/858,368 filed on Jul. 25, 2013, 61/927,424 filed on Jan. 14, 2014 and, 62/016,797 filed on Jun. 25, 2014, the disclosures of which are incorporated by reference.

FIELD OF THE INVENTION

The present invention provides new procedures and intermediates for the preparation of Perampanel.

BACKGROUND OF THE INVENTION

Perampanel, (3-(2-cyanophenyl)-5-(2-pyridyl)-1-phenyl-1,2-dihydropyridin-2-one, has the following chemical structure:

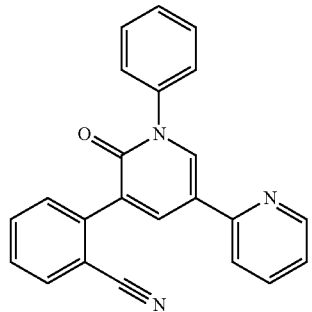

Perampanel, also referred herein as "Compound Ia", or "Ia", is a selective antagonist for the AMPA subtype of ionotropic glutamate receptors. It is developed by Eisai Co. under the trade name Fycompa®, for the treatment of epilepsy and diabetic neuropathy.

U.S. Pat. No. 6,949,571 (also referred to herein as "the '571 patent") describes Perampanel and a process for preparing it from a di-substituted pyridine. The process comprises eight synthetic steps, from which two steps require the use of metal catalyst.

The process can be illustrated by the following scheme 1.

Scheme 1:

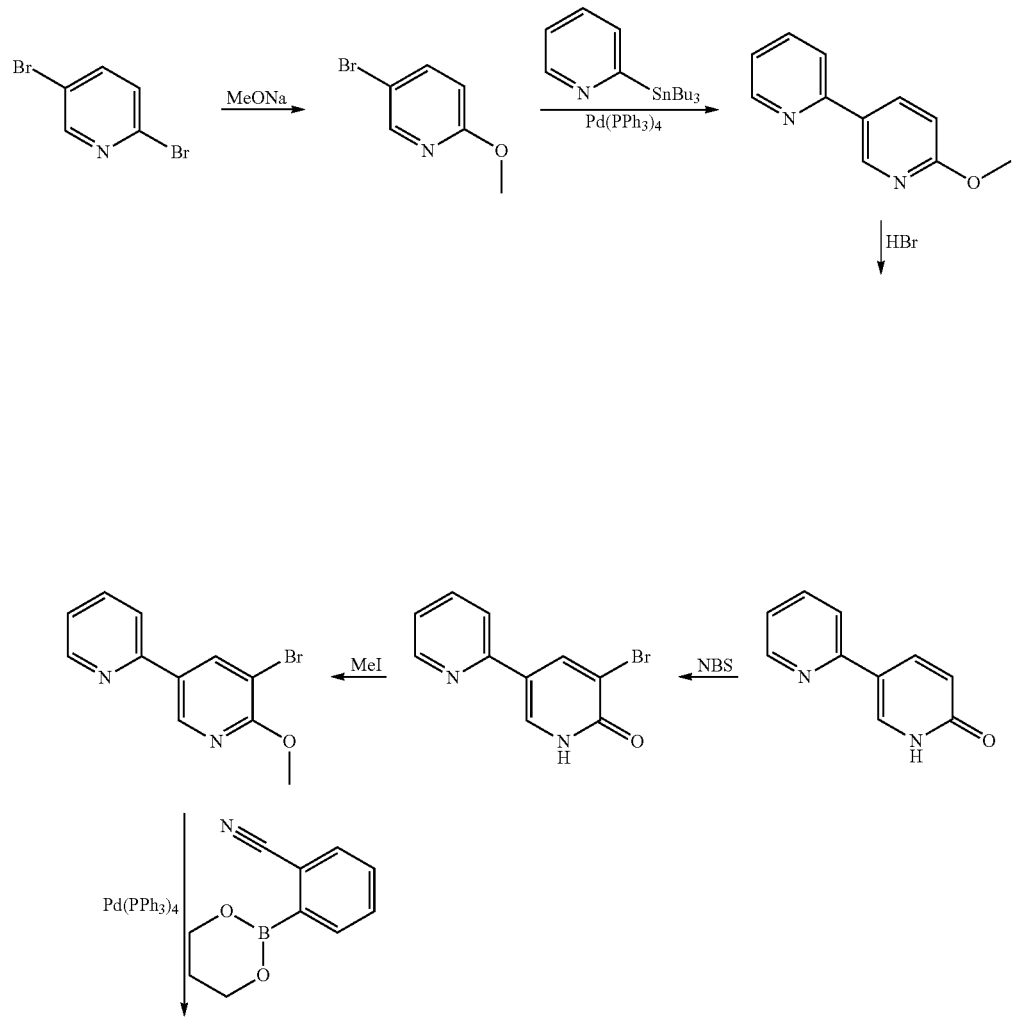

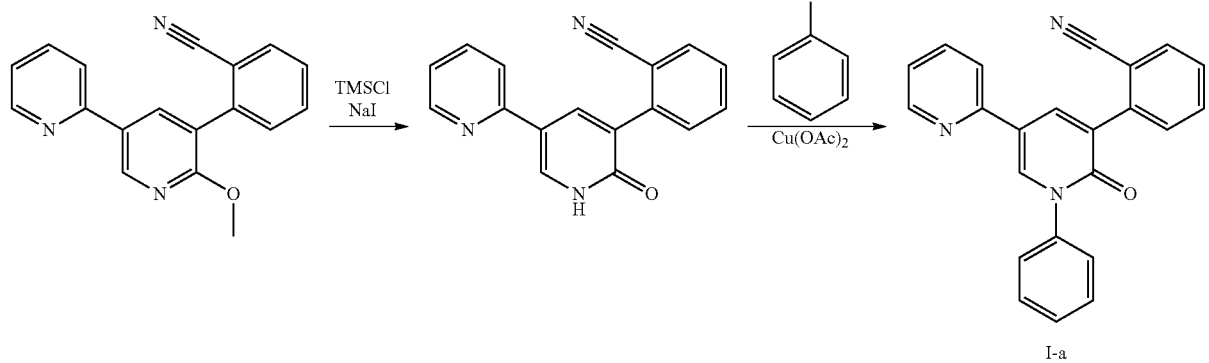

The '571 patent also describes an alternative process for preparing Perampanel derivatives, from a 2-amino-5-bromopyridine. The process comprises six synthetic steps and also comprises the use of metal catalyst. The process can be illustrated by the following scheme 2:

U.S. Pat. No. 8,304,548 (also referred to herein as "the '548 patent") describes another process for preparing Perampanel. The process is based on the eight step synthesis described in the '571 patent (scheme 1), however it doesn't utilize methyl protection of the oxygen in the 5'-bromo-6'-

Scheme 2:

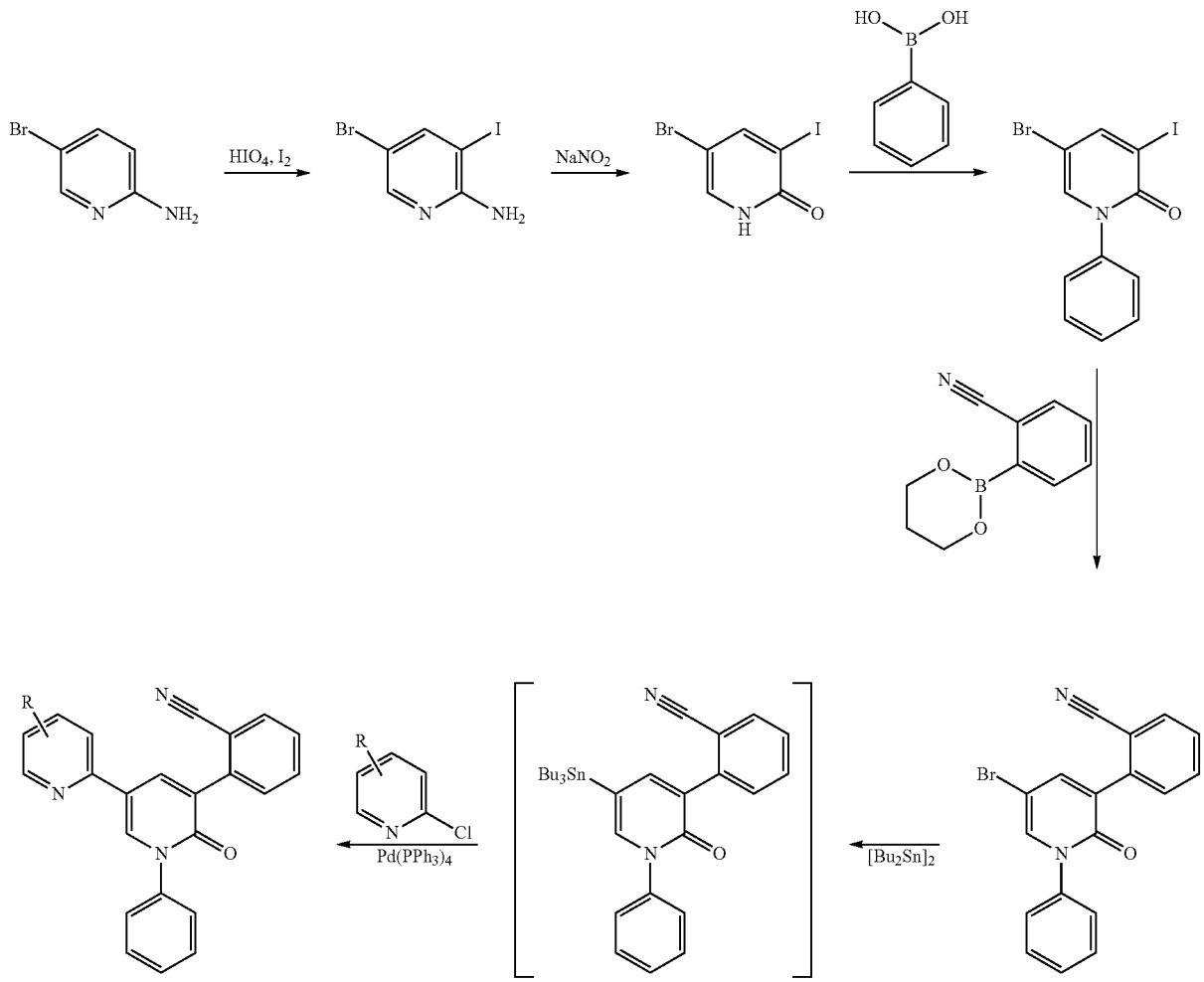

methoxy-2,3'-bipyridine intermediate prior to the coupling with the benzonitrile moiety, and its later removal. The process, which comprises six synthetic steps and the use of metal catalyst, can be illustrated by the following scheme 3.

Scheme 3:

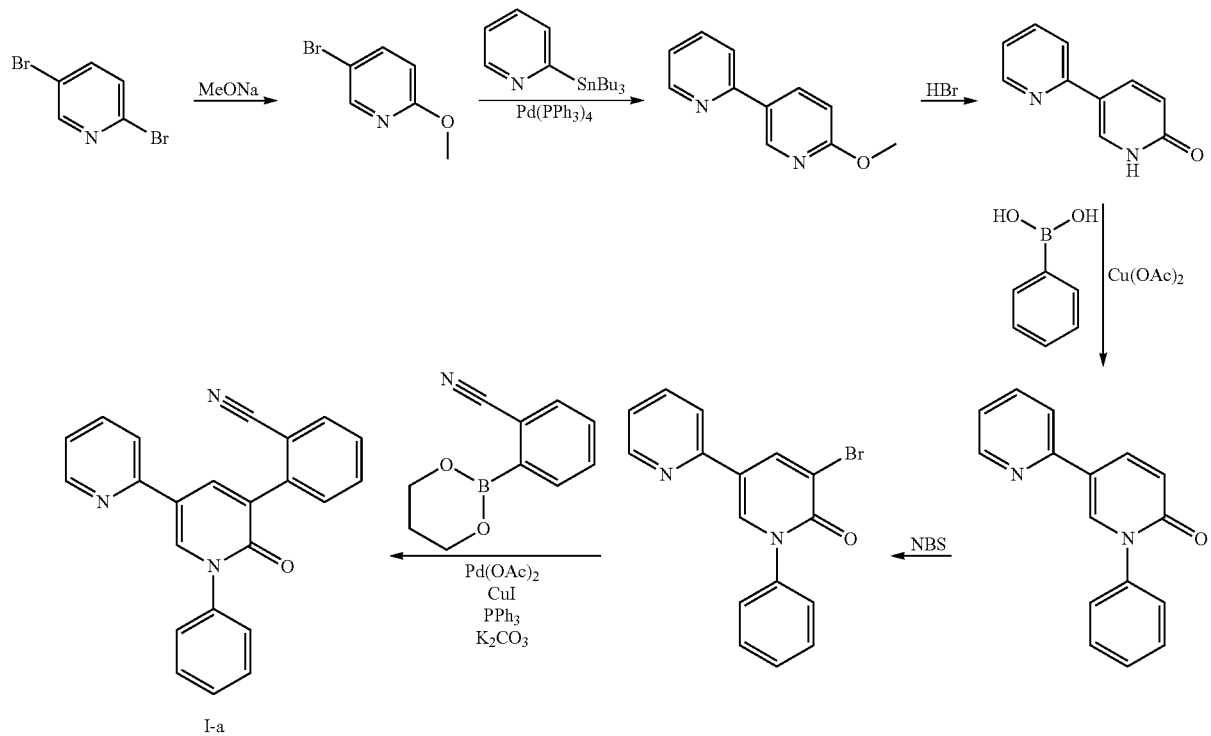

I-a

US 2010/0016603, U.S. Pat. No. 7,524,967 and US 2013/0109862 (now issued as U.S. Pat. No. 8,742,118) describe several processes for preparing the [2,3'-bipyridin]-6'(1'H)-one intermediate.

WO 2014/023576 describes the synthesis of alternative cyanophenylboronic intermediates that can be used in the above described processes for preparation of Perampanel.

The above described processes require many reaction steps and provide Perampanel in pure yield.

There is a need in the art to provide an efficient process, which provides Perampanel in high yield and quality, and that can be utilized in industrial scale.

SUMMARY OF THE INVENTION

The present invention provides intermediates useful for the synthesis of Perampanel and processes employing said intermediates for preparing Perampanel. In a first aspect, the invention relates to the use of the compounds of Formula II and salts thereof of the following structure:

Formula II

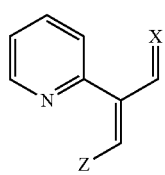

in the preparation of Perampanel, wherein:
X is oxygen or a $NR^2R^3$ group, where $R^2$ and $R^3$ are independently selected from a $C_1$-$C_{15}$ straight or branched alkyl group, a $C_1$-$C_{10}$ cycloalkyl group, an optionally substituted $C_6$-$C_{10}$ aryl group and an optionally substituted $C_7$-$C_{12}$ arylalkyl group; and Z is a leaving group. In some embodiments, Z is selected from a $NR^2R^3$ group where $R^2$ and $R^3$ are as defined above, OH, halogen, alkoxy, methanesulfonyl, or p-toluenesulfonyl.

In a second aspect, the present invention also provides the use of compounds of Formula III of the following structure:

Formula III

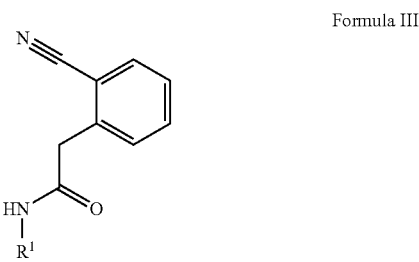

in the preparation of Perampanel; wherein $R^1$ is hydrogen or phenyl.

In a third aspect, the present invention provides isolated compounds of Formula IIa and IIb, preferably in solid form.

The compounds of Formula II and III are intermediates that can be advantageously used in the preparation of Perampanel. Accordingly, the present invention also provides a process for the preparation of Perampanel, comprising reacting the compound of Formula II and the compound of Formula III.

In a further aspect, the present invention also provides polymorphically pure crystalline form II, and process for preparation thereof.

BRIEF DESCRIPTION OF THE FIGURES

FIG. 1 shows a powder XRD pattern of crystalline Perampanel form II.

FIG. 2 shows a powder XRD pattern of crystalline compound of Formula IIa.

FIG. 3 shows a powder XRD pattern of crystalline compound of Formula IIb.

FIG. 4 shows a powder XRD pattern of crystalline compound of Formula IIIa.

FIG. 5 shows a powder XRD pattern of crystalline Perampanel form I.

FIG. 6 shows a powder XRD pattern of polymorphic pure crystalline Perampanel form II.

FIG. 7 shows a powder XRD pattern of crystalline Perampanel form II obtained in example 13.

FIG. 8 shows a powder XRD pattern of crystalline Perampanel form II obtained in example 14.

FIG. 9 shows a powder XRD pattern of crystalline Perampanel form II obtained in example 15.

DETAILED DESCRIPTION OF THE INVENTION

The present invention provides new procedures employing advantageous intermediates for the preparation of Perampanel. According to the processes of the present invention, Perampanel is obtained in high yield, of at least 40%, and high quality, i.e. in high chemical purity.

The processes described in the literature have significant disadvantages. For example, these processes are not economical, as they require many reaction steps and provide the product in low yield. Accordingly, the processes described in the literature are not suitable for industrial scale. For example, as described in the '548 patent (scheme 3) and also confirmed by the applicant of the present invention, the process reported in this patent provides the final product in at total yield of about 20-25%.

Additionally, the processes described in the literature utilize transition metal catalyst in several reaction steps, which are highly expensive and may lead to metal contamination in the final product, therefore making the process less economical.

In contrast to the prior art processes, the processes of the present invention have fewer reaction steps, do not require the use of a transition metal catalyst and are highly efficient and can be adapted to an industrial scale.

Particularly, the processes of the present invention utilize the intermediate of Formula II, particularly Formula IIa; and the intermediate of Formula III (IIa), as defined hereinafter, which can be isolated as a solid and stable compound. These advantages render the intermediate extremely useful for the manufacturing process of Perampanel, particularly at an industrial scale.

As used herein, "substantially free" is meant that the solid state forms of the present invention contain 20% (w/w) or less of polymorphs, or of a specified polymorph of Perampanel. According to some embodiments, the salts and solid state forms of the present invention contain 10% (w/w) or less, 5% (w/w) or less, 2% (w/w) or less, 1% (w/w) or less, 0.5% (w/w) or less, or 0.2% (w/w) or less of polymorphs, or of a specified polymorph of Perampanel. In other embodiments, solid state form of Perampanel of the present invention contain from 1% to 20% (w/w), from 5% to 20% (w/w), or from 5% to 10% (w/w) of any solid state forms or of a specified polymorph of Perampanel.

Depending on which other solid state forms comparison is made with, the crystalline form of Perampanel of the present invention has advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Perampanel referred to herein as being characterized by graphical data "as depicted in" or "as substantially depicted in" a Figure will thus be understood to include any crystal forms of Perampanel characterized with the graphical data having such small variations, as are well known to the skilled person, in comparison with the Figure.

As used herein, unless stated otherwise, the XRPD measurements are taken using copper Kα radiation wavelength 1.541874 Å.

As used herein, the term "isolated" in reference to the intermediates of the present invention, their salts or solid state forms thereof corresponds to a compound that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure of about 10 mbar to about 500 mbar, typically about 50 mbar.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

In one aspect, the present invention provides the use of compounds of Formula II and salts thereof of the following structure:

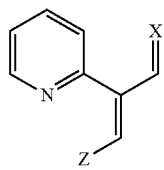

Formula II in the preparation of Perampanel, wherein:
X is oxygen or a NR²R³ group, wherein R² and R³ are independently selected from: a $C_1$-$C_{15}$ straight or branched alkyl group, a $C_1$-$C_{10}$ cycloalkyl group, an optionally substituted $C_6$-$C_{10}$ aryl group and an optionally substituted $C_7$-$C_{12}$ arylalkyl group; and Z is a leaving group. In certain embodiments, Z is preferably selected from the group consisting of a NR²R³ group where R² and R³ are as defined above, OH, halogen, alkoxy, methanesulfonyl, and p-toluenesulfonyl.

As indicated above, compounds of formula II may be used in the processes of the invention in the form of salt. Suitable salts may include, but are not limited to: halides, for example chloride or bromide; other non-coordinating anion types, such as hexafluorophosphate, tetrafluoroborate or perchlorate; or other suitable inorganic or organic salts. Hexafluorophosphate or chloride salts of Formula II are preferred intermediates that can be used in the processes for preparing Perampanel.

In some embodiments, X and Z are NR²R³ groups where R² and R³ are both alkyl groups, preferably methyl groups. Preferably, the compound is defined herein as a compound of Formula IIa of the following structure:

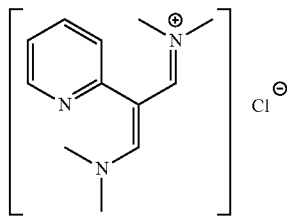

Formula IIa

In other embodiments, X and Z are as indicated above, and the compound of Formula II is in the form of hexafluorophosphate, of the following Formula IIb:

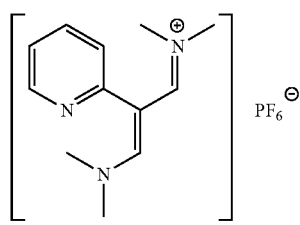

Formula IIb

In certain embodiments, the present invention provides isolated compounds of Formula IIa and IIb, preferably they are in solid form.

In preferred embodiments, the compounds of Formula IIa and IIb are crystalline compounds.

The present invention encompasses a crystalline compound of Formula IIa, characterized by data selected from one or more of the following: X-ray powder diffraction pattern having peaks at 10.5, 11.3, 14.9, 17.2, 18.3, 18.9, 19.2, 19.8, 22.1 and 27.9 degrees two theta±0.2 degrees two theta; an X-ray powder diffraction pattern as depicted in FIG. 2; and combinations of these data.

The present invention also encompasses a crystalline compound of Formula IIb, characterized by data selected from one or more of the following: X-ray powder diffraction pattern having peaks at 9.6, 10.7, 13.5, 14.5, 16.3, 16.7, 17.2, 19.2, 20.0 and 21.1 degrees two theta±0.2 degrees two theta; an X-ray powder diffraction pattern as depicted in FIG. 3; and combinations of these data.

The compound of Formula II can be prepared by reacting 2-(pyridin-2-yl)acetic acid hydrochloride of the following formula:

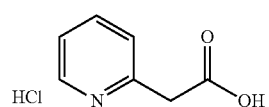

Formula IV and an acyl halide in the presence of dimethylformamide ("DMF").

When X and Z are NR²R³ groups where R² and R³ are both methyl group, i.e. the compound of Formula IIa is obtained, the compound of Formula IV is reacted with an acyl halide, such as phosphorous oxychloride, and DMF.

In another aspect, the present invention also provides the use of a compound of Formula III of the following structure:

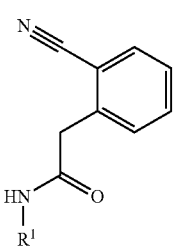

Formula III in the preparation of Perampanel; wherein R¹ is hydrogen or phenyl.

When R¹ is phenyl, the compound is defined herein as a compound of Formula IIIa of the following structure:

Formula IIIa

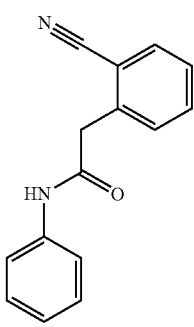

The present invention also provides the isolated compound of Formula IIIa, preferably in solid form, more preferably in crystalline form, and its use in a process for preparing Perampanel.

The present invention also encompasses a crystalline compound of Formula IIIa, characterized by data selected from one or more of the following: X-ray powder diffraction pattern having peaks at 5.8, 11.5, 12.0, 15.1, 15.8, 20.4, 21.5, 23.4, 24.2 and 26.0 degrees two theta±0.2 degrees two theta; an X-ray powder diffraction pattern as depicted in FIG. 4; and combinations of these data.

When $R^1$ is hydrogen, the compound is defined herein as a compound of Formula IIIb of the following structure:

Formula IIIb

The compound of formula III can be prepared by reacting 2-(2-cyanophenyl)acetic acid of the following formula:

Formula V and the corresponding substituted amine or aqueous ammonia. The reaction can be carried out in the presence of thionyl chloride. Alternatively, the reaction can be carried out in the presence of acyl halide, preferably oxalylchloride and a catalytic amount of N,N-dimethylformamide (DMF).

When $R^1$ is phenyl, i.e. the compound of Formula IIIa, then the compound of formula V is reacted with aniline, preferably at the above-described conditions.

When $R^1$ is hydrogen, i.e. the compound of Formula IIIb, then the compound of formula V is reacted with aqueous ammonia solution, preferably at the above described conditions.

The above described compounds of Formula II and III, particularly the compounds of Formula IIa, IIb and IIIa, can be reacted in a process for preparing Perampanel.

The present invention therefore also provides a process for the preparation of Perampanel comprising reacting the compound of formula II and the compound of Formula III.

This process of the present invention can be illustrated by the following scheme 4.

Scheme 4:

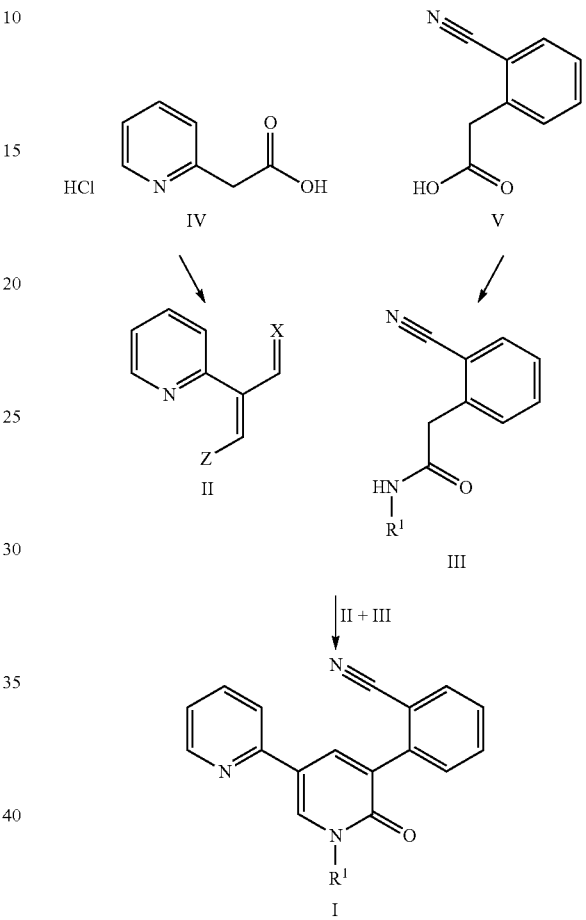

The reaction is typically carried out in the presence of a suitable solvent. Suitable solvents may include, for example, tetrahydrofurane, methyltetrahydrofurane, acetonitrile, dimethylformamide, N-methylacetamide, N,N-dimethylacetamide, dimethylsulfoxide, toluene, methanol, ethanol, butanol, ethyl acetate, n-butyl acetate and mixtures thereof.

The reaction may be performed in the presence of suitable base, such as alkali metal hydrides, like sodium hydride, potassium hydride; alkali metal amides, for example, lithium diisopropylamide; metal oxides, such as lithium methoxide, sodium methoxide, potassium methoxide, sodium ethoxide, potassium tert-butoxide, lithium oxide; basic amines, such as 1,8-diazabicyclo[5.4.0]undec-7-ene ("DBU"); or carbonates, such as, potassium carbonate, cesium carbonate. The reaction can be accomplished at about room temperature. Alternatively, the reaction can be done while heating, with a temperature ranging from about 40° C. to about 130° C.

When the compound of Formula IIIb is used in the reaction, then the process for preparing Perampanel will include an additional arylation step. The arylation can be done, for example, by reacting the obtained intermediate from the previous step with phenylboronic acid. The reaction can be carried out in the presence of a copper salt, for example copper acetate.

The present invention further provides a process for preparing crystalline Perampanel form II.

As used herein, the term crystalline Perampanel form II relates to crystalline Perampanel characterized by data selected from one or more of the following: X-ray powder diffraction pattern having peaks at 4.6, 8.9, 12.0, 15.8, 20.5, 24.3 and 26.9 degrees two theta±0.2 degrees two theta; X-ray powder diffraction pattern having peaks at 8.9, 15.8 and 24.3 degrees two theta±0.2 degrees two theta; an X-ray powder diffraction pattern as depicted in FIG. 1; and combinations of these data.

The said process comprises crystallizing Perampanel from a mixture of solvent and anti-solvent. Typically the solvent is selected from dimethyl sulfoxide (DMSO), acetonitrile and tetrahydrofuran; and the anti-solvent is selected from heptane, isopropanol and methyl tert-butyl ether (MTBE). Typically, the process comprises dissolving Perampanel in the above described solvents and adding the anti-solvent, such as isopropanol, to obtain a mixture from which Perampanel form II precipitates. The dissolution in the solvent can be done while heating to a suitable temperature, for example, when using DMSO the heating is to a temperature of about 40° C. to about 50° C. or when using THF the heating to a temperature about 50° C. to about 65° C. After a solution is obtained, it can be cooled down, preferably to a temperature of about room temperature. To aid to the precipitation step, the mixture can be further cooled down after the addition of the anti-solvent, such as isopropanol, preferably in an ice-bath, or the hot Perampanel solution can be added to a cold anti-solvent at temperature about −15° C. to about 10° C.

The above described process can for example be carried out using crystalline Perampanel form I as a starting material in the crystallization process.

As used herein, the term crystalline Perampanel form I relates to crystalline Perampanel characterized by data selected from one or more of the following: X-ray powder diffraction pattern having peaks at 4.7, 7.8, 9.4, 10.3, 14.2, 15.0, 16.0, 19.1, 20.4 and 22.4 degrees two theta±0.2 degrees two theta; an X-ray powder diffraction pattern as depicted in FIG. 5; and combinations of these data.

The present invention encompasses crystalline Perampanel form II that is polymorphically pure.

As used herein, the term polymorphically pure relates to crystalline Perampanel form II having not more than 10%, more preferably not more than 5%, most preferably not more than 1% by weight of any other crystalline form of Perampanel, particularly Perampanel form I, form V or hydrated form. The polymorphic purity of crystalline Perampanel form II can be determined by measuring the content of the above described crystalline forms by PXRD. For example, a skilled person would measure the content of crystalline form I in crystalline Perampanel form II by detecting and quantifying the characteristic peaks of form I described in the literature (absent in form II). Accordingly, the content of crystalline Perampanel form V in crystalline Perampanel form II will be measured by detecting and quantifying the described characteristic peaks of form V (absent in form II); and the content of Perampanel hydrate will be measured by detecting and quantifying the described characteristic peaks of Perampanel hydrate (absent in form II).

The characteristic peaks of crystalline Perampanel form I used for the above described measurement can be selected from the following list of peaks at about: 4.7, 7.8, 10.3, 14.2, 15.1, 17.7, 19.1, 20.4 and 22.4 degrees two theta±0.2 degrees two theta; particularly, the characteristic peaks used for the above described measurement are selected from the peaks at about: 7.8, 10.3 and 19.1 degrees two theta±0.2 degrees two theta.

The characteristic peaks of crystalline Perampanel form V used for the above described measurement may be selected from the following list of peaks at about: 6.1, 8.0, 10.0, 12.2, 12.9, 14.3, 16.7, 18.4, 18.8, 20.7 and 22.1 degrees two theta±0.2 degrees two theta; particularly, the characteristic peaks used for the above described measurement are selected from the peaks at about: 6.1, 8.0, 10.0, 12.9, 16.7 and 22.1 degrees two theta±0.2 degrees two theta.

The characteristic peaks of crystalline Perampanel hydrate used for the above described measurement may be selected from the following list of peaks at about: 7.8, 11.7, 12.5, 13.7, 14.6, 17.5, 19.1, 20.0, 21.1 and 21.4 degrees two theta±0.2 degrees two theta; particularly, the characteristic peaks used for the above described measurement are selected from the peaks at about: 7.8, 11.7, 12.5, 17.5, 19.1 and 21.4 degrees two theta±0.2 degrees two theta.

The polymorphically pure Perampanel form II may be characterized by the X-ray powder diffraction pattern depicted in FIG. 6.

Compared to other polymorphic forms of Perampanel, the polymorphically pure Perampanel form II may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, and bulk density.

The solid-state properties of a drug substance may affect a number of properties of the drug substance. For example, it can have a significant influence on the apparent solubility and dissolution rate of the drug substance, thereby potentially having an effect on a drug product bioavailability and bioequivalence. The solid state characteristics of a drug substance in crystalline form may also have an effect on the manufacture of the final drug product (flowability, hygroscopicity, storage stability, stability during formulation, etc.). Polymorphic conversion and the presence of a different polymorphic form as an "impurity" or by-product in a form used for pharmaceutical composition or formulation may likewise negatively affect the dissolution rate or apparent solubility of the formulated drug product. In addition, if another polymorph has, for example, a different hygroscopicity or hydration state, the molecular weight of the drug will change, which is clearly undesirable when preparing the final formulation Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Powder X-Ray Diffraction ("PXRD") Method:

Powder X-ray Diffraction was performed on an X-Ray powder diffractometer PanAlytical X'pert Pro; CuKα radiation ($\lambda$=1.541874 Å); X'Celerator detector with active length 2.122 degrees 2-theta; laboratory temperature 25±2°

C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement Parameters:

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

EXAMPLES

Example 1

1,1,5,5-Tetramethyl-3-(2-pyridyl)-1,5-diazapentadienium chloride (II-a)

Phosphorus(V) oxychloride (16.10 mL, 0.173 mol) was charged to 250 mL two-necked flask equipped with a thermometer. The content of the flask was cooled in an ice-water bath. Afterwards, dry dimethylformamide (DMF) (20.07 mL, 0.259 mol) was added drop-wise under inert atmosphere while keeping the temperature of the mixture below 10° C. After the addition was completed the mixture was left to warm up to room temperature and stirred for 10 minutes, followed by addition of compound IV (10 g, 0.058 mol) in one portion. The mixture was heated to 80-85° C. for 3-4 hours. The reaction mixture was then cooled to 10° C. and acetonitrile (30 mL) was added with stirring. Afterwards, the mixture was cooled in an ice-water bath and a solution of $K_2CO_3$ (50 g) in water (70 mL) was added drop-wise to obtain a pH 7-8 while keeping the temperature below 10° C. Afterwards, the mixture was stirred overnight at room temperature. The formed suspension was filtered and the filtration cake was washed with acetonitrile (2×10 mL). Combined filtrates were poured into a separation funnel. The organic phase was separated and dried over silica gel (0.5 g), the solvent was then replaced by isopropanol (iPrOH) by adding and evaporating of iPrOH in several portions (3×100 mL), then concentrated at 50° C. and reduced pressure (50-200 mbar) to a volume of approximately 25 mL. The residue was heated to 55° C. and acetone (180 mL) was added drop-wise. The mixture was then cooled to room temp, stirred for 5 minutes, then cooled in an ice-water bath for 40 minutes and filtered. The filtration cake was washed with acetone (2×15 mL) and dried at 80° C. for 5 hours to get the title compound as a slightly brownish solid (6.9 g, yield 50%).

Example 2

1,1,5,5-Tetramethyl-3-(2-pyridyl)-1,5-diazapentadienium chloride (II-a)

Phosphorus(V) oxychloride (10.74 mL, 0.115 mol) was charged to a 100 mL jacketed reactor equipped with a thermometer. The content of the reaction vessel was cooled to 5° C. Afterwards, dry dimethylformamide (DMF) (16.06 mL, 0.207 mol) was added drop-wise under an inert atmosphere while keeping the temperature of the mixture below 15° C. After the addition was completed the mixture was left to warm up to 25° C. and stirred for 5 minutes, followed by addition of compound IV (8 g, 0.046 mol) and dry toluene (8 mL). The mixture was heated to 95° C. for 3 hours. The reaction mixture was then cooled to 10° C., and acetonitrile (40 mL) was added with stirring and then the mixture was cooled to 5° C. Afterwards, a solution of $K_2CO_3$ (30 g) in water (30 mL) was added drop-wise to obtain a pH 7-8 while keeping the temperature below 15° C. The mixture was then stirred overnight at room temperature. The formed suspension was filtered and the filtration cake was washed with acetonitrile (2×30 mL). The combined filtrates were poured into a separation funnel. The organic phase was separated and dried over silica gel (2.0 g). The solvent was then replaced by isopropanol (iPrOH) by adding and evaporating of iPrOH in several portions (3×80 mL), then the mixture was concentrated at 40-45° C. under reduced pressure (50-200 mbar) to a volume of approximately 16 mL. The residue was heated to 50° C. and acetone (144 mL) was added drop-wise. The mixture was then cooled to room temperature, stirred for 5 minutes, then cooled to −7° C., and was stirred at the same temperature for 20 minutes. Then, the product was filtered and the filtration cake was washed with cold acetone (2×10 mL) and vacuum dried at 80° C. for 5-7 hours to get the title compound as a pale brown solid (8.8 g, yield 79%) in HPLC purity 99.5%. The product was analyzed by PXRD, the PXRD pattern is shown in FIG. 2.

Example 3

1,1,5,5-Tetramethyl-3-(2-pyridyl)-1,5-diazapentadienium hexafluorophosphate (II-b)

Phosphorus(V) oxychloride (10.74 mL, 0.115 mol) was charged to a 100 mL jacketed reactor equipped with a thermometer. The content of the reaction vessel was cooled to 5° C. Afterwards, dry dimethylformamide (DMF) (48.17 mL, 0.622 mol) was added drop-wise under an inert atmosphere while keeping the temperature of the mixture below 20° C. After the addition was completed the mixture was left to warm up to 20-25° C. and stirred for 5 minutes, followed by addition of compound IV (8 g, 0.046 mol) and dry toluene (8 mL). The mixture was heated to 90° C. for 3.5 hours. Afterwards, the reaction mixture was cooled to 5° C. A solution of $K_2CO_3$ (30 g) in water (90 mL) was then added drop-wise while keeping the temperature below 15° C. The mixture was then stirred overnight at room temperature. The formed suspension was filtered and the filtration cake was washed with water (20 mL). The filtrates were combined and then solid potassium hexafluorophosphate (12.72 g, 0.069 mol) was added thereto. The mixture was stirred at room temperature for 10 minutes, and then cooled to −8° C. stirred at the same temperature for 30 minutes. The product was filtered and the filtration cake was washed with cold water (2×15 mL) and dried on filter with suction for 2-3 hours to get the title compound as a pale brownish solid (8.8 g, yield 79%) in HPLC purity 99.8%. The product was analyzed by PXRD, and the PXRD pattern is shown in FIG. 3.

Example 4

1,1,5,5-Tetramethyl-3-(2-pyridyl)-1,5-diazapentadienium hexafluorophosphate (II-b)

Compound II-a (0.5 g, 2.1 mmol) was dissolved in a mixture of acetonitrile (1.5 mL) and water (2.5 mL) at room temperature. Afterwards, a suspension of potassium hexaflourophosphate (0.691 g, 3.8 mmol) was added thereto. The mixture was stirred at room temperature for 20 minutes, then at 0-5° C. for 30 minutes and filtered. The product was washed with water and dried at room temperature to give compound II-b as a pale brown solid (0.503 g, 69%).

Example 5

N-Phenyl-2-(2-cyanophenyl)acetamide (III-a)

Compound V (5.00 g, 0.031 mol) was dissolved in dry dichloromethane (150 mL). Afterwards, oxalylchloride (5.25 mL, 0.062 mol) was added, followed by a catalytic amount of N,N-dimethylformamide (about 0.05 mL). The mixture was then stirred at room temperature under an inert atmosphere for 70 minutes and evaporated to dryness. The oily residue was dissolved in dry dichloromethane (80 mL) and cooled in an ice-water bath. Aniline (5.56 mL, 0.062 mol) was then drop-wise added to the dichloromethane solution. The mixture was stirred at 0-5° C. for 20 minutes and then for additional 40 minutes at room temperature. After the reaction was completed, 1M HCl (100 mL) was added slowly, followed by addition of ethylacetate (EtOAc) (100 mL) with stirring. The organic phase was then separated and the water phase was extracted by EtOAc (2×150 mL). The combined organic extracts were washed with saturated $NaHCO_3$ solution (2×100 mL), dried over $MgSO_4$ and evaporated to dryness. The crude product was crystallized from iPrOH/heptane to give the title compound as an off-white solid (6.5 g, 88%).

Example 6

N-Phenyl-2-(2-cyanophenyl)acetamide (III-a)

Compound V (50.0 g, 0.310 mol) was charged to a 1 L jacketed reactor and suspended in dry ethyl acetate (700 mL). Thionyl chloride (27.2 mL, 0.372 mol) was added in one portion and the mixture was then heated at 45° C. for 2 hours. The mixture was then concentrated at a temperature 40-50° C. and reduced pressure (50-200 mbar) to a volume of approximately 600 mL. Afterwards, the residue was cooled to 0° C., followed by addition of aniline (62.2 mL, 0.682 mol) dissolved in ethyl acetate (150 mL). The rate of the addition was controlled to keep the temperature of the reaction mixture below 25° C. After the addition was finished, the mixture was stirred at room temperature for 30 minutes, followed by addition of 2.5% aqueous NaCl (200 mL) and heating the obtained mixture to 40-45° C. with stirring. When all of the solid material was dissolved, the water phase was separated. The solvent in the remaining phase was replaced by isopropanol (iPrOH) by adding and evaporating of iPrOH in several portions (4×100 mL), then the mixture was concentrated at 40-45° C. under reduced pressure (50-200 mbar) to a volume of approximately 400 mL, followed by addition of water (200 mL). The mixture was cooled to 0° C., stirred at the same temperature for 30 minutes and filtered. The obtained product was then washed with 50% aqueous iPrOH (180 mL) and dried in an inert atmosphere at room temp overnight to give compound III-a as an off-white solid (67.1 g, yield 92%) with a HPLC purity of ~92%. The product was analyzed by PXRD, and the PXRD pattern is shown in FIG. 4.

Example 7

2-(2-Cyanophenyl)acetamide (III-b)

Compound V (5.00 g, 0.031 mol) was dissolved in dry dichloromethane (150 mL). Afterwards, oxalylchloride (5.25 mL, 0.062 mol) was added, followed by a catalytic amount of N,N-dimethylformamide (about 0.05 mL). The mixture was then stirred at room temperature under an inert atmosphere for 70 minutes and evaporated to dryness. The oily residue was dissolved in dry tetrahydrofuran (THF) (50 mL) and added to an aqueous ammonia (26%, 100 mL) cooled in an ice-water bath. The mixture was stirred at 0-5° C. for 20 minutes and then additional 40 minutes at room temperature. After the reaction was completed, the mixture was poured into a separation funnel and extracted by EtOAc (2×250 mL). The combined organic extracts were washed with saturated $NaHCO_3$ solution (2×100 mL), dried over $MgSO_4$ and evaporated to dryness. The crude product was crystallized from iPrOH/hexane to give the title compound as an off-white solid (3.41 g, 69%).

Example 8

3-(2-cyanophenyl)-5-(2-pyridyl)-1-phenyl-1,2-dihydropyridin-2-one (I-a)

Compound II-a (0.107 g, 0.4 mmol), compound III-a (0.100 g, 0.4 mmol) and lithium methoxide (0.034 g, 0.9 mmol) were suspended in dry dimethyl sulfoxide (DMSO) (1.5 mL) and heated at 65-70° C. for 50 minutes. The mixture was then left to cool down to room temperature, and then diluted with 50% aqueous methanol (MeOH) (15 mL) and stirred at room temperature for 15 minutes. The formed suspension was then cooled in an ice-water bath for 30 minutes and filtered. The filtration cake was washed with cold 50% aqueous MeOH (2×1 mL) and dried at room temperature to give the title compound as a pale yellow solid (0.080 g, 54%).

Example 9

Crystallization of Compound I-a

Compound I-a (0.250 g) was dissolved in DMSO (2.5 mL) at a temperature of 45-50° C. The obtained solution was then cooled to room temperature followed by addition of iPrOH (15 mL) and cooling the mixture in an ice-water bath for 30 minutes and subsequent filtration. The product was dried overnight at room temperature, and tested by PXRD. Crystalline Perampanel form II was obtained.

Example 10

3-(2-cyanophenyl)-5-(2-pyridyl)-1-phenyl-1,2-dihydropyridin-2-one (I-a)

Compound II-b (10.6 g, 0.030 mol), compound III-a (7.00 g, 0.030 mol) and lithium methoxide (2.48 g, 0.065 mol) were suspended in dry dimethyl sulfoxide (DMSO) (28 mL) and heated at 55° C. for 35 minutes. Afterwards, n-butyl acetate (nBuOAc) (130 mL) was added and the mixture was heated to 80° C., followed by slow addition of 2.5% aqueous NaCl (50 mL). The water phase was separated at temperature of about 80-85° C. and the remaining organic phase was cooled down to 5° C., was stirred at the same temperature and filtered. The filtration cake was washed with cold nBuOAc (3×20 mL). The obtained crude product was crystallized from nBuOAc to give the title compound as an off-white to yellowish solid (6.23 g, 60%) in HPLC purity >99.8%.

Example 11

3-(2-cyanophenyl)-5-(2-pyridyl)-1-phenyl-1,2-dihydropyridin-2-one (I-a, Perampanel)

Compound II-b (10.6 g, 0.030 mol) and compound III-a (7.00 g, 0.030 mol) were suspended in dry dimethyl sulfoxide (DMSO) (17.5 mL). The mixture was then heated to 40-45° C. followed by addition of sodium ethoxide (23.2 mL of 21% solution in EtOH, 0.062 mol). The reaction mixture was stirred at 40-45° C. for 30 min. Afterwards, ethyl acetate (EtOAc) (150 mL) was added and the mixture was heated to 75° C., followed by slow addition of 10% aqueous NaCl (80 mL) to keep the temp. between 65-70° C. The water phase was separated at a temperature of about 68-70° C. The residual water was removed by concentration of the organic phase to an approximate volume of 105 mL by distillation at a temperature of about 55-62° C. under reduced pressure. Afterwards, the mixture was cooled down to 5° C., then stirred at the same temperature for 30 min. and filtered. The filtration cake was washed with cold (0-5° C.) EtOAc (3×20 mL). The obtained product was dried on a filter with suction for 2 hours and then left standing overnight at room temp. to give title compound as yellowish solid (7.45 g, 72%) in HPLC purity >99.5%. The product was tested by PXRD—crystalline Perampanel form I was obtained, and the PXRD pattern is shown in FIG. 5.

Example 12

3-(2-cyanophenyl)-5-(2-pyridyl)-1-phenyl-1,2-dihydropyridin-2-one (I-a, Perampanel)

Compound II-b (31.9 g, 0.091 mol) and compound III-a (20.0 g, 0.085 mol) were suspended in dry n-butyl acetate (nBuOAc) (400 mL). The mixture was then heated to 65-70° C. followed by addition of sodium ethoxide (47.4 mL of 21% solution in EtOH, 0.127 mol) in one portion. The reaction mixture was stirred at 65-70° C. for 30 min. Afterwards, water (150 mL) was added slowly to keep the temperature between 65-70° C. The water phase was separated at temperature of about 65-70° C. and then 10% aqueous NaCl (120 mL) was slowly added to the remaining organic phase. Temperature during the addition was kept between 65-70° C. The water phase was then separated at temperature of about 65-70° C. The remaining nBuOAc phase was concentrated by vacuum distillation to approximate volume of ~400 mL. Afterwards, the mixture was diluted with additional nBuOAc (100 mL) and concentrated again by distillation at temperature about 55-85° C. under reduced pressure to remove the residual water from the organic phase. The mixture was then cooled down to −5° C., then stirred at the same temperature for 30 minutes. and filtered. The filtration cake was washed with cold (5° C.) methyl tert-butyl ether (3×120 mL) and dried at room temp. under inert atmosphere. The obtained product was then dissolved in nBuOAc (25 volumes) at temperature 110-115° C., treated with activated charcoal (5% w/w) at the same temperature and filtered. The obtained solution was then cooled to temperature about 85-90° C. followed by addition of Perampanel form I seeds. The mixture was then cooled down to −5° C., then stirred at the same temperature for 30 min. and filtered. The filtration cake washed with cold (5° C.) methyl tert-butyl ether (2×120 mL), dried on filter with suction for 2 hours and then left standing overnight at room temp. to give title compound as yellowish solid (17.7 g, 60%) in HPLC purity >99.5%. The product was tested by PXRD—crystalline Perampanel form I was obtained.

Example 13

Crystallization of Compound I-a (Perampanel)

Perampanel form I (0.500 g) was dissolved in DMSO (4 mL) by stirring at a temperature of 45-50° C. The obtained solution was then cooled to room temperature without stirring, followed by addition of iPrOH (20 mL) in one portion. The mixture was then stirred and cooled in an ice-water bath for 30 minutes and filtered. The filtration cake was washed with cold iPrOH (2×1.5 mL). The product was dried overnight at room temperature to give the title compound (0.287 g) in HPLC purity >99.5%, and was tested by PXRD. Crystalline Perampanel form II was obtained, and the PXRD pattern is shown in FIG. 7.

Example 14

Crystallization of Compound I-a (Perampanel)

Perampanel form I (0.500 g) was dissolved in acetonitrile (4 mL) by stirring at a temperature of 80° C. The obtained solution was then cooled to room temperature without stirring, followed by addition of iPrOH (15 mL) in one portion. The mixture was then stirred and cooled in an ice-water bath for 15 minutes followed by addition of iPrOH (10 mL), stirring for additional 15 minutes and subsequent filtration. The filtration cake was washed with cold iPrOH (2×1.5 mL). The product was dried overnight at room temperature to give the title compound (0.225 g) in HPLC purity >99.5%, and was tested by PXRD. Crystalline Perampanel form II was obtained, and the PXRD pattern is shown in FIG. 8.

Example 15

Crystallization of Compound I-a (Perampanel)

Perampanel form I (0.500 g) was dissolved in THF (5 mL) by stirring at reflux. The obtained solution was then cooled to room temperature without stirring, followed by addition of iPrOH (20 mL) in one portion. The mixture was then stirred and cooled in an ice-water bath for 30 minutes and filtered. The filtration cake was washed with cold iPrOH (2×1.5 mL). The product was dried overnight at room temperature to give the title compound (0.384 g) in HPLC purity >99.5%, and was tested by PXRD. Crystalline Perampanel form II was obtained, and the PXRD pattern is shown in FIG. 9.

Example 16

Crystallization of Compound I-a (Perampanel)

Perampanel form I (20.0 g) was dissolved in THF (560 mL) while stirring at 60-65° C. The obtained solution was then added to cold (about −15° C.) methyl tert-butyl ether. The temperature during the addition of the Perampanel solution was kept at about −15° C. to 5° C. The mixture was then stirred at −15° C. for 120 minutes and filtered. The filtration cake was washed with cold methyl tert-butyl ether (600 mL). The product was dried overnight under a flow of nitrogen gas to give the title compound (9.14 g) in HPLC purity >99.5%, and was tested by PXRD. Pure Crystalline Perampanel form II was obtained, and the PXRD pattern is shown in FIG. 6.

Example 17

Crystallization of Compound I-a (Perampanel)

Perampanel form I (200.0 g) was dissolved in THF (5600 mL) by stirring at 60-65° C. The obtained solution was then added to cold heptane (about −15° C.). The temperature during the addition of Perampanel solution was kept at about −15° C. to 0° C. The mixture was then stirred at −15° C. for 25 minutes and filtered. The filtration cake was washed with cold heptane (6000 mL). The product was dried overnight under a flow of nitrogen gas to give the title compound (183.2 g) in HPLC purity >99.5% and was tested by PXRD. Crystalline Perampanel form II was obtained.

Example 18

3-(2-cyanophenyl)-5-(2-pyridyl)-1,2-dihydropyridin-2-one (I-b)

Compound II-a (0.107 g, 0.4 mmol), compound III-b (0.116 g, 0.4 mmol) and lithium methoxide (0.034 g, 0.9 mmol) are suspended in dry DMSO (1.5 mL) and heated at 65-70° C. for 50 minutes. The mixture is then left to cool down to room temperature and is subjected to column chromatography in hexane/ethyl acetate gradient elution mode.

Example 19

3-(2-cyanophenyl)-5-(2-pyridyl)-1,2-dihydropyridin-2-one (I-b)

Compound II-b (1.112 g, 3.2 mmol), compound III-b (0.500 g, 3.1 mmol) and cesium carbonate (2.136 g, 6.6 mmol) were suspended in dry DMSO (5.0 mL) and heated at 55-60° C. for 3.5 hours. The mixture is then left to cool down to room temperature followed by addition of water (30 mL). The mixture was then stirred at room temperature for 5 minutes, then cooled to 0-5° C. for 30 minutes and filtered. The filtration cake was washed with water (3×5 mL) and methyl tert-butyl ether (1×5 mL) and dried at room temperature overnight. The obtained red-brownish solid was used directly into the next synthetic step (described in Example 21).

Example 20

3-(2-cyanophenyl)-5-(2-pyridyl)-1-phenyl-1,2-dihydropyridin-2-one (I-a)

Compound I-b (0.100 g, 0.4 mmol), phenylboronic acid (0.110 g, 0.9 mmol), copper acetate (0.010 g, 0.05 mmol) and pyridine (0.1 mL, 0.9 mmol) are suspended in N,N-dimethylformamide (2 mL) and are heated to 50° C. After the reaction is completed the mixture is concentrated and subjected to column chromatography in hexane/ethyl acetate gradient elution mode (hexane/EtOAc 2/1 EtOAc) to give the title product.

Example 21

3-(2-cyanophenyl)-5-(2-pyridyl)-1-phenyl-1,2-dihydropyridin-2-one (I-a)

Compound I-b that was prepared according to Example 19 (1.19 g), phenylboronic acid (1.062 g, 8.7 mmol), copper (II) acetate monohydrate (0.087 g, 0.4 mmol) and pyridine (1.05 mL, 13.1 mmol) were charged into 50 mL round-bottom flask and suspended in acetone (24 mL). The mixture was heated with stirring at 40-45° C. for 7 hours under ambient atmosphere (no inert gas). After the reaction was completed the mixture was partitioned between EtOAc (70 mL) and brine (150 mL). The organic phase was then dried over MgSO$_4$, evaporated to dryness and subjected to column chromatography in hexane/ethyl acetate gradient elution mode to give the title product (0.370 g).

I claim:

1. A process for preparing Perampanel, comprising reacting the compound of Formula II or salts thereof of the following structure:

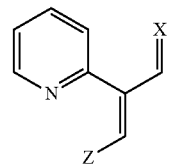

Formula II wherein:

X is oxygen or a NR$^2$R$^3$ group, wherein R$^2$ and R$^3$ are independently selected from: a C$_1$-C$_{15}$ straight or branched alkyl group, a C$_1$-C$_{10}$ cycloalkyl group, an optionally substituted C$_6$-C$_{10}$ aryl group and an optionally substituted C$_7$-C$_{12}$ arylalkyl group; and Z is a leaving group;

and the compound of Formula III of the following structure:

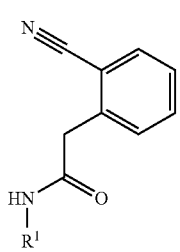

Formula III wherein R$^1$ is hydrogen or phenyl and wherein the reaction is carried out in the presence of a solvent.

2. The process of claim 1, wherein the reaction is carried out in the presence of a base.

3. The process of claim 1, wherein the compound of Formula III is in the form of the compound of Formula IIIb,

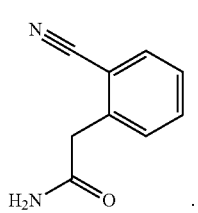
Formula IIIb
and the process further comprises an arylation step carried out in the presence of a solvent to obtain Perampanel.
4. The process of claim 1 wherein the solvent is n-butyl acetate, ethyl acetate, or dimethyl sulfoxide.
5. The process of claim 2 wherein the base is sodium ethoxide.
* * * * *